United States Patent [19]

Freudenberger

[11] Patent Number: 5,081,291

[45] Date of Patent: Jan. 14, 1992

[54] PROCESS FOR MANUFACTURE OF 3,3',4,4'-BIPHENYLTETRACARBOXYLIC ACID

[75] Inventor: John H. Freudenberger, Elkton, Md.

[73] Assignee: E. I. Du Pont de Nemours and Company, Wilmington, Del.

[21] Appl. No.: 586,158

[22] Filed: Sep. 21, 1990

[51] Int. Cl.⁵ .................. C07C 51/353; C07C 51/377
[52] U.S. Cl. ...................... 562/481; 560/96; 562/480
[58] Field of Search ............ 562/480, 481; 560/96

[56] References Cited

U.S. PATENT DOCUMENTS

| | | | |
|---|---|---|---|
| 4,292,435 | 9/1981 | Itatani et al. | 560/96 |
| 4,338,456 | 6/1982 | Itatani et al. | 560/96 |
| 4,720,576 | 1/1988 | Wada et al. | 562/481 |
| 4,727,185 | 2/1988 | Shoji et al. | 562/481 |

FOREIGN PATENT DOCUMENTS 50-031148 10/1975 Japan.
62-212328 9/1987 Japan.

*Primary Examiner*—Jose G. Dees
*Assistant Examiner*—Vera C. Clarke

[57] ABSTRACT

A process for the preparation of 3,3',4,4'-biphenyltetracarboxylic acid salt by the dehalodimerization of a 4-halophthalic acid salt. The process uses hydroxylamine or one of its salts as the reducing agent in an alkaline solution, preferably of pH 10 or above, and palladium catalyst. The reaction is carried out between 50° and 150° C.

10 Claims, No Drawings

PROCESS FOR MANUFACTURE OF 3,3',4,4'-BIPHENYLTETRACARBOXYLIC ACID

FIELD OF THE INVENTION

This invention relates to a method for producing 3,3',4,4'-biphenyltetracarboxylic acid, from 4-halophthalic acid salts. More particularly it relates to a method for producing 3,3',4,4'-biphenyltetracarboxylic acid by the condensation of 4-halophthalic acids using hydroxylamine as the reducing agent in the presence of a noble metal catalyst.

BACKGROUND OF THE INVENTION

A number of processes are known for the preparation of 3,3',4,4'-biphenyltetracarboxylic acid salts (BPTA) which are important starting materials for the preparation of heat resistant polyimide resins. It is known that biphenyl compounds can be produced by reductive coupling of an aromatic halide. For example in U.S. Pat. No. 4,727,185, a method is disclosed in which a 4-halophthalic acid is condensed in the presence of a noble metal catalyst, a formic acid salt, and a small amount of alcohol. However relatively large amounts of expensive noble metal catalyst are required to obtain good yields and quality, as well as long reaction times. In U.S. Pat. No. 4,720,576 a process for preparing BPTA is described starting from 4-chlorophthalic acid using carbon monoxide in the presence of a supported palladium catalyst. The reaction requires pressures of 20-70 psig, large amounts of catalyst, and comparatively longer reaction times. Other references use reducing agents such as formaldehyde or methanol, but yields of final product are impractical for a commercial process.

It is known from U.S. Pat. Nos. 4,292,435 and 4,338,456 that biphenyl tetracarboxylic esters can be produced by oxidative coupling of orthophthalic esters by passing molecular oxygen through the molten compound in the presence of a noble metal catalyst. This process requires high temperatures (100°-300° C.) and can only be run to low conversion, necessitating the handling of a large recycle stream. It also requires the use of a diester as a starting material.

SUMMARY OF THE INVENTION

It is a primary object of the present invention to provide an economical and commercially viable process for the preparation of 3,3',4,4'-biphenyltetracarboxylic acid salts from a 4-halophthalic acid, in which the reaction can take place in a short time using a minimum amount of expensive noble metal catalyst and in good yields. The above objects can be obtained by using hydroxylamine as the reducing agent, and adding it to an aqueous solution of a salt of a 4-halophthalic acid in the presence of a noble metal catalyst. According to this process BPTA can be obtained in high yield using less than one tenth of the catalyst required in the prior art processes and with shorter reaction times.

DETAILED DESCRIPTION OF THE INVENTION

As the 4-halophthalic acid that can be used in the present invention, there can be mentioned 4-chlorophthalic acid, 4-bromophthalic acid, or 4-iodophthalic acid. Alkali metal salts of these acids, such as the sodium, potassium or lithium salts also may be used. Derivatives which are easily hydrolyzed by aqueous base to 4-halophthalic acid salts, such 4-halophthalic anhydrides or esters may also be used. The 4-bromo derivatives, 4-bromophthalic acid, the sodium and potassium salts of 4-bromophthalic acid, and 4-bromophthalic anhydride are especially preferred. Use of 4-chlorophthalic acid requires much longer reaction times and gives lower yields of product. Use of 4-iodophthalic acid is not competitive economically.

4-Halophthalic acids, or salts thereof, frequently contain amounts of 3-halophthalic acid, 4,5-dihalophthalic acid and phthalic acid. These impurities do not affect the process, as any resulting by-products are easily separated from the desired 3,3',4,4'-biphenyltetracarboxylic acid.

As the aqueous base in the present invention, there can be mentioned alkali metal hydroxides, such as sodium hydroxide, potassium hydroxide, and lithium hydroxide, alkali metal carbonates such as sodium carbonate and potassium carbonate, and alkaline earth hydroxides and carbonates, such as calcium hydroxide and calcium carbonate. Tetraalkylammonium hydroxides, such as tetramethylammonium hydroxide may also be used. For economy and ease of handling, sodium hydroxide and potassium hydroxide are especially preferred. It is preferred that sufficient base is used in the reaction mixture containing 4-halophthalic acid, or derivative thereof, to maintain the pH of the solution at a value of 10 or greater throughout the reaction. The required amount of base can be added all at once in the beginning of the reaction, or can be added as needed during the reaction. At values of pH less than 10, reduced yields of 3,3',4,4'-biphenyltetracarboxylic acid are obtained. Thus enough base must be used to convert the 4-halophthalic acid, or derivative thereof, to the dibasic salt of the 4-halophthalic acid, and to neutralize any acid formed during the reaction. More specifically, starting with one equivalent of 4-bromophthalic acid, or 4-bromophthalic anhydride and reducing with 0.5 equivalent of an acid salt of the reducing reagent, the preferred amount of base is 3.5 eq or greater.

As the catalyst used in the present invention, there can be mentioned palladium black, or palladium supported on a carrier, such as palladium (Pd) on carbon, Pd on alumina, Pd on calcium carbonate, Pd on silica and Pd on barium sulfate. A Pd on carbon catalyst is especially preferred. The preferred palladium content in the supported catalyst is 1-10% by weight.

The amount of catalyst used is critical to the economic value of the process. The smaller the amount used the better, although larger amounts are not detrimental to the reaction. The amount of catalyst is determined by its activity and the time desired to carry out the reaction. In the present invention the amount of metal catalyst can range from 0.001 to 0.5% weight Pd on the final product produced, with the preferred range being from 0.01 to 0.1%. If a smaller amount than 0.001% is used the yield is low, and higher amounts than 0.1% make the process less economical.

Hydroxylamine, which is the reducing agent in the present invention can be added directly as an aqueous solution, or used in the form of one of its acid salts. Such salts can include the hydrochloride, hydrobromide, acetate, sulfate, or other soluble salt. Under the reaction conditions hydroxylamine reacts almost instantaneously upon addition to give either the desired product, or unproductive self-decomposition, i.e., disproportionation. In the presence of very high catalyst loadings, the hydroxylamine can be added as quickly as one can control the rate of gas evolution. At lower, more economical catalyst loadings, slower addition rates maximize the use of hydroxylamine by minimizing disproportionation. Thus, there are a variety of conditions available for optimization of the process; in the amount of catalyst used, the addition rate of the hydroxylamine, the amount of hydroxylamine added, and the reaction temperature. A minimum of 0.5 equivalent of hydroxylamine is required to complete the reaction under optimum conditions. In practice some hydroxylamine is lost to disproportionation, therefore the use of 0.75 equivalents or more is preferred.

The dehalodimerization to produce BPTA is carried out in aqueous solution at temperatures between 50° and 150° C., with from 70° to 110° C. being preferred. The 4-halophthalic acid is dissolved in aqueous base, heated to reaction temperature, catalyst added, and the hydroxylamine salt solution added over the desired period of time. One can select optimum conditions, i.e., catalyst loading and addition rate, to fit the equipment available with a wide degree of flexibility. At the end of the reaction the catalyst is removed, and the product is isolated by techniques known to those skilled in the art, such as treatment with a strong mineral acid.

EXAMPLES OF THE INVENTION

Example 1

A 100 g sample of 4-bromophthalic anhydride (0.440 mol) was dissolved in 275 ml of water containing 75 g of sodium hydroxide (1.9 mol). The solution was treated with 0.50 g of 5% palladium on carbon catalyst (50% water wet; 5% Pd dry basis; 0.013 g Pd). The mixture was then heated to 95° C. An aqueous solution of 27 g hydroxylamine sulfate (0.16 mole) in 75 ml of water was added dropwise over a period of 3 hr. Gas evolution was observed during the addition. After complete addition, the mixture was filtered to remove the catalyst. The filtrate was then added to 125 ml of concentrated hydrochloric acid (1.39 mol) diluted with 250 ml of water at 95° C. The precipitated product was collected via filtration. The white, crystalline powder was washed three times with 200 ml of 1% hydrochloric acid at 85° C. The wet cake was dried for 16 hours at 110°-120° C. in vacuo with nitrogen purge. The yield of 3,3',4,4'-biphenyltetracarboxylic acid was 65.0 g (89%). This corresponds to a catalyst loading of 0.019 wt % Pd per weight of product.

Example 2

Example 1 was repeated except 36 g of hydroxylamine sulfate (0.22 mol) were used. The yield of 3,3',4,4'-biphenyltetracarboxylic acid was 63.0 g (87%).

Example 3

Example 1 was repeated except 18 g of hydroxylamine sulfate (0.11 mol) were used. The yield of 3,3',4,4'-biphenyltetracarboxylic acid was 56.6 g (78%).

Example 4

Example 1 was repeated except 23 g of hydroxylamine chloride (0.33 mol) were used in place of hydroxylamine sulfate. The yield of 3,3',4,4'-biphenyltetracarboxylic acid was 63.7 g (88%).

Example 5

Example 1 was repeated except 110 g of potassium hydroxide (2.0 mol) were used in place of sodium hydroxide. The yield of 3,3',4,4'-biphenyltetracarboxylic acid was 61.0 g (84%).

Example 6

Example 1 was repeated except the reaction temperature was 75° C. The yield of 3,3',4,4'-biphenyltetracarboxylic acid was 52.5 g (72%).

Example 7

Example 1 was repeated except the reaction mixture was refluxed (~108° C.). The yield of 3,3',4,4'-biphenyltetracarboxylic acid was 55.5 g (76%).

Example 8

Example 1 was repeated except that the hydroxylamine sulfate solution was added over a period of 20 minutes. The yield of 3,3',4,4'-biphenyltetracarboxylic acid was 45.7 g (63%).

Example 9

Example 1 was repeated except that the hydroxylamine sulfate solution was added over a period of 20 minutes, and the catalyst loading was increased to 2.5 g (50% wet; 5% Pd dry basis; 0.063 g Pd). The yield of 3,3',4,4'-biphenyltetracarboxylic acid was 64.2 g (88%). This corresponds to a catalyst loading of 0.098 wt % per weight of product.

Example 10

Example 1 was repeated except that finely divided palladium metal was used as the catalyst in place of palladium on carbon. The palladium metal was generated in situ by adding 0.080 ml of a 20% palladium solution (200 g Pd metal per liter of solution as $PdCl_2$, 0.016 g Pd) to the reaction mixture. Deep black palladium metal formed immediately upon addition of the hydroxylamine sulfate. The yield of 3,3',4,4'-biphenyltetracarboxylic acid was 57.3 g (79%). This corresponds to a catalyst loading of 0.028 wt % Pd per weight of product.

Comparative Example

Use of sodium formate as a reducing agent was repeated using the same catalyst loading and reaction time as in Example 1 given above. The concentrations of reactants are the same as reported in U.S. Pat. No. 4,727,185. The yield was 13%.

A 100 g sample of 4-bromophthalic anhydride (0.44 mol) was dissolved in 275 ml of water containing 74 g of potassium hydroxide (1.3 mol). The solution was treated with 30 g of sodium formate (0.44 mol), 18 ml of methanol (0.44 mol), and 0.50 g of 5% palladium on carbon catalyst (50% water wet; 5% Pd dry basis; 0.013 g Pd). The mixture was heated to 95° C. for 3 hours. The reaction mixture was then filtered to remove the catalyst. The filtrate was added to 175 ml of concentrated hydrochloric acid (1.95 mol) diluted with 250 ml of water at 95° C. The precipitated product was isolated, washed and dried as in Example 1. The yield of 3,3',4,4'-biphenyltetracarboxylic acid was 9.2 g (13%).

I claim:

1. A process for the preparation of 3,3',4,4'-biphenyltetracarboxylic acid salt by the dehalodimerization of a 4-halophthalic acid salt, which comprises adding an aqueous solution of hydroxylamine or one of its salts selected from the group consisting of hydrochloride, hydrobromide, acetate or sulfate salt to an alkaline solution of an alkali metal or tetraalkylammonium salt of 4-halophthalic acid in the presence of a palladium catalyst in an amount varying from 0.001 to 0.5 weight percent palladium based on an alkali metal or tetraalkylammonium salt of 3,3',4,4'-biphenyltetracarboxylic acid produced, at temperatures of between 50° C. and 150° C.

2. A process of claim 1 wherein the reaction is carried out at pH 10 or greater.

3. A process of claim 2 wherein the alkali metal or tetraalkylammonium salt of the 4-halophthalic acid is a salt of 4-chlorophthalic acid, 4-iodophthalic acid or 4-bromophthalic acid.

4. A process of claim 3 wherein the 4-halophthalic salt is a sodium or potassium salt of 4-bromophthalic acid.

5. A process of claim 4 wherein the amount of palladium catalyst varies from 0.01 to 0.1 weight percent palladium based on 3,3',4,4'-biphenyltetracarboxylic acid salt produced.

6. The process of claim 5 wherein a minimum of 0.5 equivalent, based on 4-bromophthalic salt of hydroxylamine is used.

7. The process of claim 6 wherein the reaction is carried out at 70° to 110° C.

8. The process of claim 1 wherein the catalyst loading is about 0.02% and the addition rate of 0.75 equivalent of said hydroxylamine is about 3 hours.

9. The process of claim 1 or claim 8 wherein the palladium catalyst is palladium black or palladium supported on a carrier selected from the group consisting of carbon, alumina, calcium carbonate, silica or barium sulfate.

10. The process of claim 9 wherein the palladium content is 1-10 wt % palladium on carbon.

* * * * *